United States Patent [19]

Druzgala et al.

[11] Patent Number: 6,114,344
[45] Date of Patent: Sep. 5, 2000

[54] LONG-ACTING LOCAL ANESTHETICS

[75] Inventors: Pascal Druzgala, Santa Rosa; Peter G. Milner, Los Altos Hills, both of Calif.

[73] Assignee: Aryx Therapeutics, Los Altos Hills, Calif.

[21] Appl. No.: 09/356,283

[22] Filed: Jul. 16, 1999

Related U.S. Application Data

[60] Provisional application No. 60/093,018, Jul. 16, 1998.

[51] Int. Cl.[7] ...................... A61K 31/435; A61K 31/135
[52] U.S. Cl. ............................................ 514/277; 514/646
[58] Field of Search ..................................... 514/277, 646

[56] References Cited

U.S. PATENT DOCUMENTS

| | | | |
|---|---|---|---|
| 4,562,060 | 12/1985 | Broberg et al. | 424/28 |
| 4,618,490 | 10/1986 | De Marco | 424/80 |
| 5,563,153 | 10/1996 | Mueller et al. | 514/305 |
| 5,942,543 | 8/1999 | Ernst | 514/537 |

OTHER PUBLICATIONS

Wang, Ging Kuo, Marina Vladimirov, Hao Shi, Wai Man Mok, Johann G. Thalhammer, Douglas C. Anthony (1998) "Structure—Activity Relation of N–alkyl Tetracaine Derivatives as Neurolytic Agents for Sciatic Nerve Lesions" *Anesthesiology* 88(2):417–428.

Wang, G.K., M. Vladimirov, C. Quan, W.M. Mok, J.G. Thalhammer, D.C. Anthony (1996) "N–Butyl Tetracaine as a Neurolytic Agent for Ultralong Sciatic Nerve Block" *Anesthesiology* 85(6):1386–1394.

Buchi, J.X. and Perlia.(1971) In: *Local Anesthetics* vol. 1, International Encyclopedia of Pharmacology and Therapeutics, Sect. 8, Lechat, P., ed, Pergamon Press Ltd., Oxford, pp 39–130 (no copy is enclosed).

*Primary Examiner*—Raymond Henley, III
*Attorney, Agent, or Firm*—Saliwanchik, Lloyd & Saliwanchik

[57] ABSTRACT

The subject invention concerns novel compounds that are useful as long-acting local anesthetics. The compounds are N-acyl derivatives of the compound known as tetracaine.

1 Claim, 6 Drawing Sheets

Structure

Structure

Structure

Structure

Structure

LONG-ACTING LOCAL ANESTHETICS

CROSS-REFERENCE TO A RELATED APPLICATION

This application claims priority from provisional application U.S. S No. 60/093,018, filed Jul. 16, 1998.

BACKGROUND OF THE INVENTION

Local anesthetics are drugs that block nerve impulse generation and conduction when applied locally to nerve tissue in appropriate concentrations. They act on any part of the nervous system and on every type of nerve fiber. A local anesthetic can cause both sensory and motor paralysis in the area where they are applied. Many kinds of compounds interfere with conduction, but they often permanently damage the nerve cell. The advantage of a good local anesthetic is that its action is reversible and is followed by essentially complete recovery of the nerve function with no evidence of structural damage.

A good local anesthetic should combine several properties; it should not be irritating to the tissue to which it is applied, nor should it cause any permanent damage to nerve structure. Also, its systemic toxicity should be low. Therefore, the therapeutic index is an important factor in evaluating novel local anesthetics. Since this can vary greatly, there is a constant search for new, more effective, and safer agents.

It is also important that the onset of anesthesia should be short, but that the anesthetic action last long enough for surgical procedure to take place, yet not so long as to entail an extended period of recovery. Occasionally, a local anesthetic action lasting for days or even weeks is desirable, such as in the control of chronic pain. Unfortunately, the available agents for long-term pain control have high local toxicity, resulting in neurolysis with necrosis of the surrounding tissues. Such toxicity may result in complete paralysis if it occurs in the vicinity of the spinal cord.

Most of the useful local anesthetics contain hydrophobic and hydrophilic domains that are generally separated by an intermediate alkyl chain. The hydrophilic group is usually a tertiary amine, the hydrophobic portion is usually aromatic. In almost all cases, linkage to the aromatic ring is of the ester or amide type. Changes in any part of the molecule alter the anesthetic potency of the compound as well as its toxicity. For example, increasing the length of the intermediate alkyl chain results in more potent anesthetic properties, but also in increased toxicity. These relationships have been reviewed by Buchi and Perlia (Buchi, J. X., Perlia [1971] In: Local Anesthetics, Vol. 1, International Encyclopedia of Pharmacology and Therapeutics, Sect. 8, Lechat, P., ed, Pergamon Press Ltd., Oxford, pp 39–130).

Tetracaine is a known local anesthetic (FIG. 1). Tetracaine derivatives of the N-alkyl type have been described in the scientific literature (Wang, G. K., M. Vladimirov, H. Shi, W. M. Mok, J. G. Thalhammer, D. C. Anthony [1998] Anesthesiology 88:417–428). These derivatives have very long-lasting anesthetic properties and the highest homologs of the series are neurolytic, normally an unwanted form of local toxicity, which the authors claim as a desirable property for use in destruction of pathogenic regions that produce pain (Wang, G. K., M. Vladimirov, C. Quan, W. M. Mok, J. G. Thalbammer, D. C. Anthony [1996] Anesthesiology 85(6):1386–1394), as for example in sciatic nerve.

BRIEF SUMMARY OF THE INVENTION

The subject invention concerns novel compounds which are useful as long-acting local anesthetics. A further aspect of the subject invention pertains to methods of using the novel compounds to achieve long-acting local anesthesia.

In a specific embodiment, the subject invention concerns N-acyl derivatives of tetracaine, which, unexpectedly and advantageously, have valuable anesthetic properties not possessed by the parent compound, or its other known derivatives, e.g., N-alkyl derivatives. The discovery of the N-acyl derivatives of the subject invention brings about certain advantages over the N-akyl types. For example, the presence of an N-acyl group provides the molecule with an amide moiety that is readily hydrolyzed within the mammalian body. Hydrolysis produces either the initial tetracaine molecule or N-butyl p-aminobenzoic acid, a known metabolite of tetracaine. This is not an option in the N-alkyl series.

The compounds of the subject invention are particularly advantageous because they are not neurolytic. The N-acyl series of this invention is, therefore, well suited for chronic pain management requiring long term administration of local anesthetics. The compounds of the subject invention are also very well suited for administration prior to local surgical procedures such as in dental or maxillofacial surgery or in ocular surgery.

DETAILED DISCLOSURE OF THE INVENTION

Figure 1:
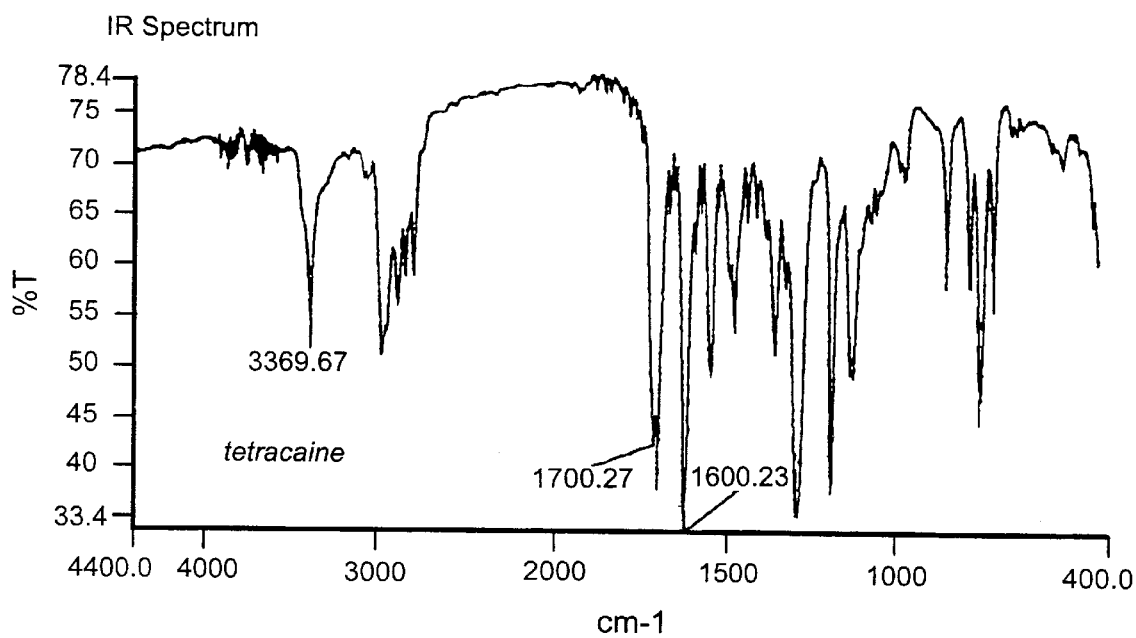
FIG. 1 Tetracaine IR spectrum and structure.
Figure 1:
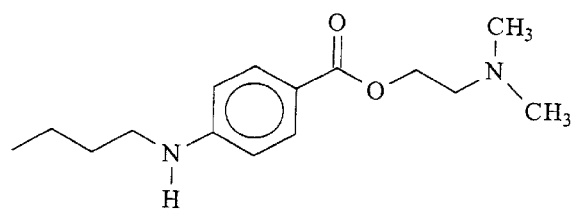
Figure 2:
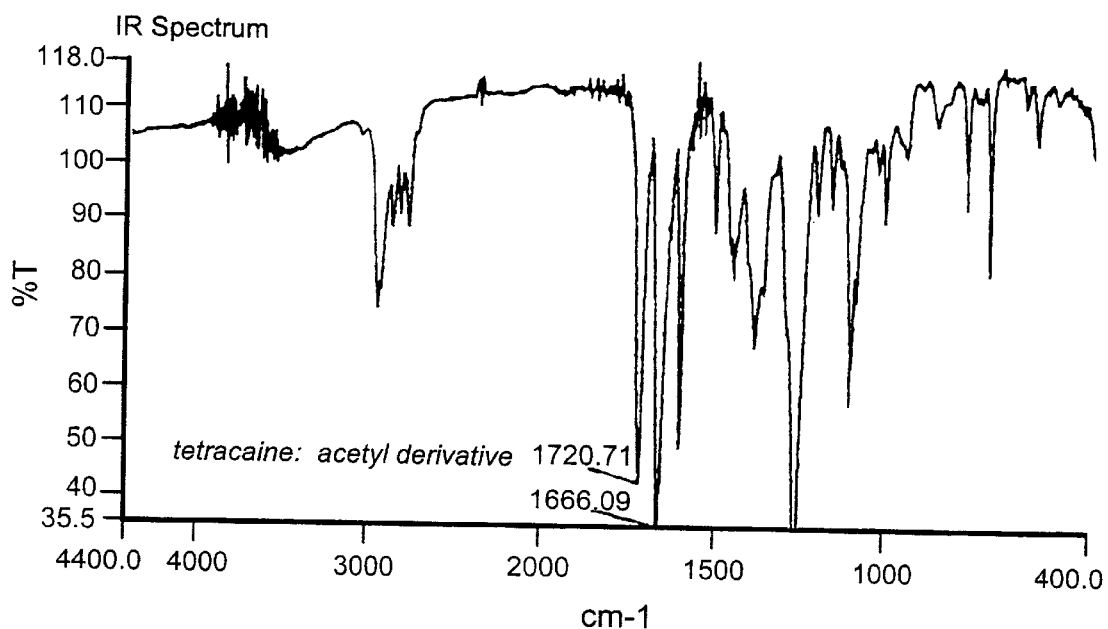
FIG. 2 Acetyl derivative IR spectrum and structure.
Figure 2:
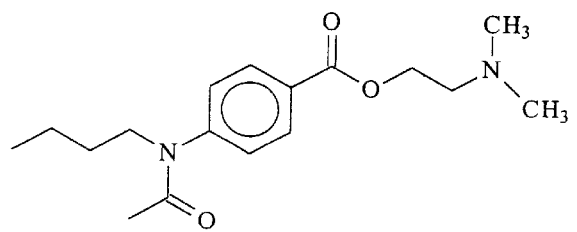
Figure 3:
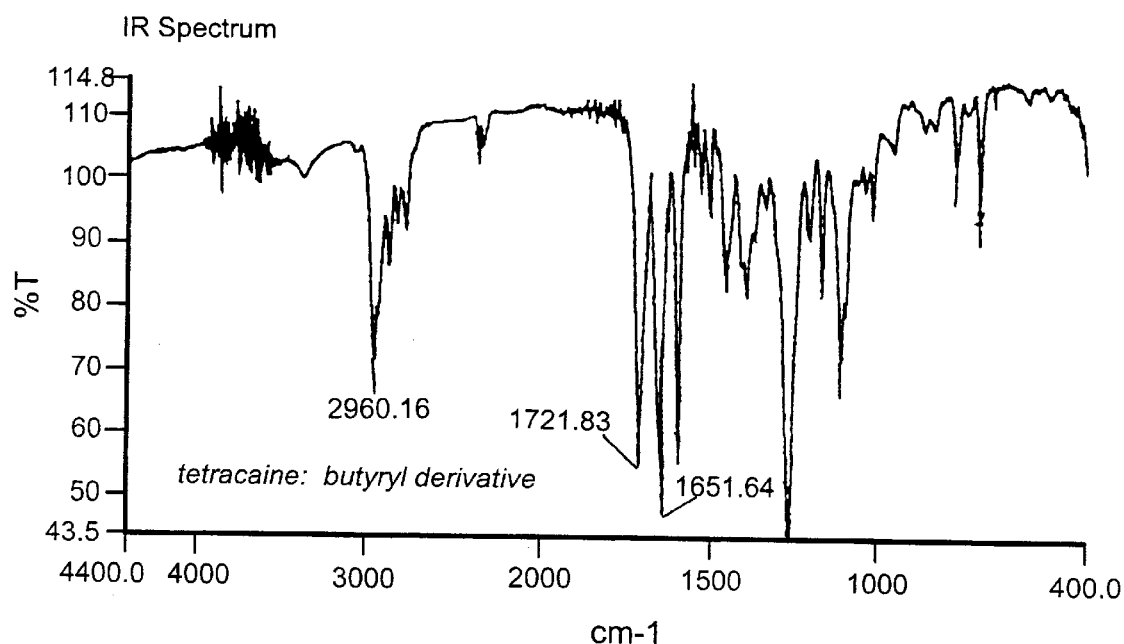
FIG. 3 Butyryl derivative IR spectrum and structure.
Figure 3:
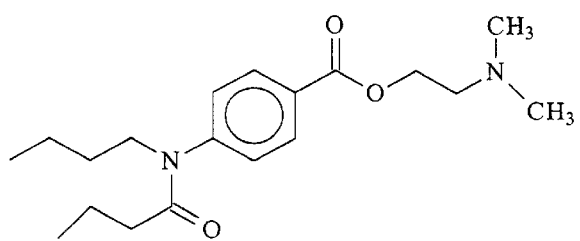
Figure 4:
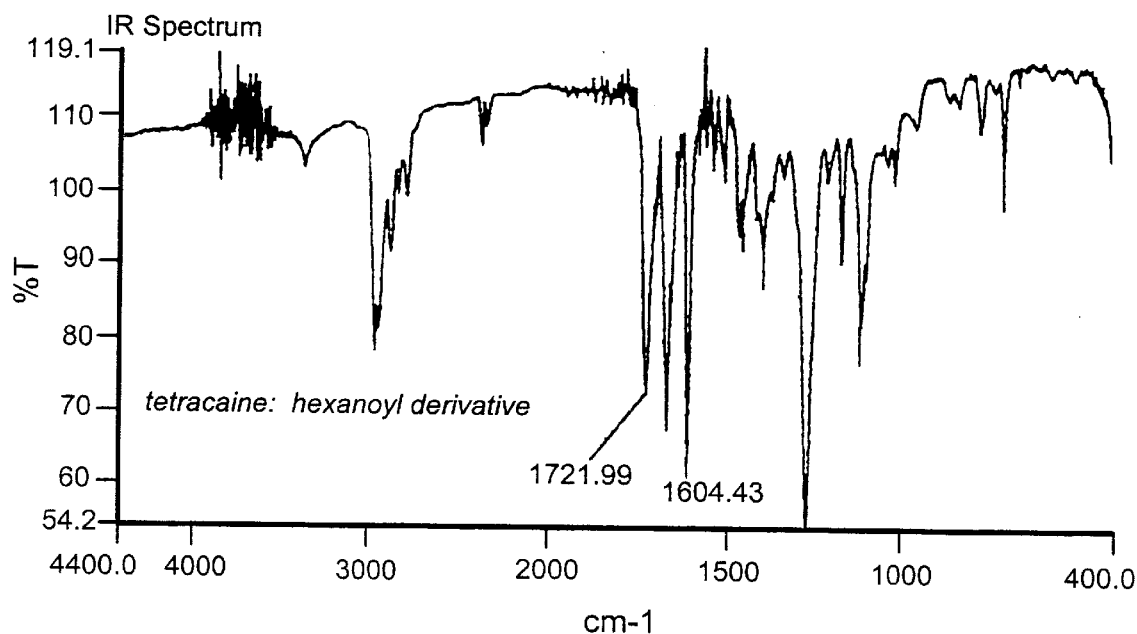
FIG. 4 Hexanoyl derivative IR spectrum and structure.
Figure 4:
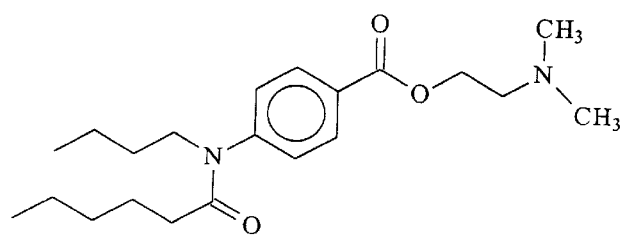
Figure 5:
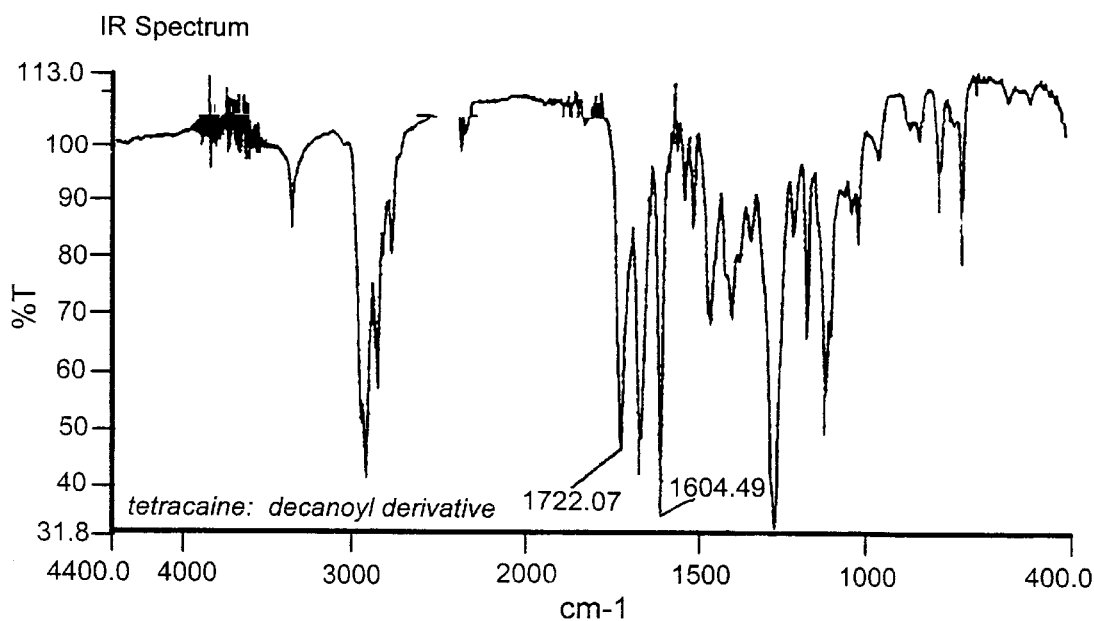
FIG. 5 Decanoyl derivative IR spectrum and structure.
Figure 5:
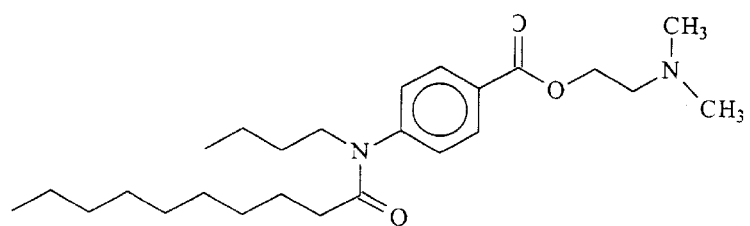
Figure 6:
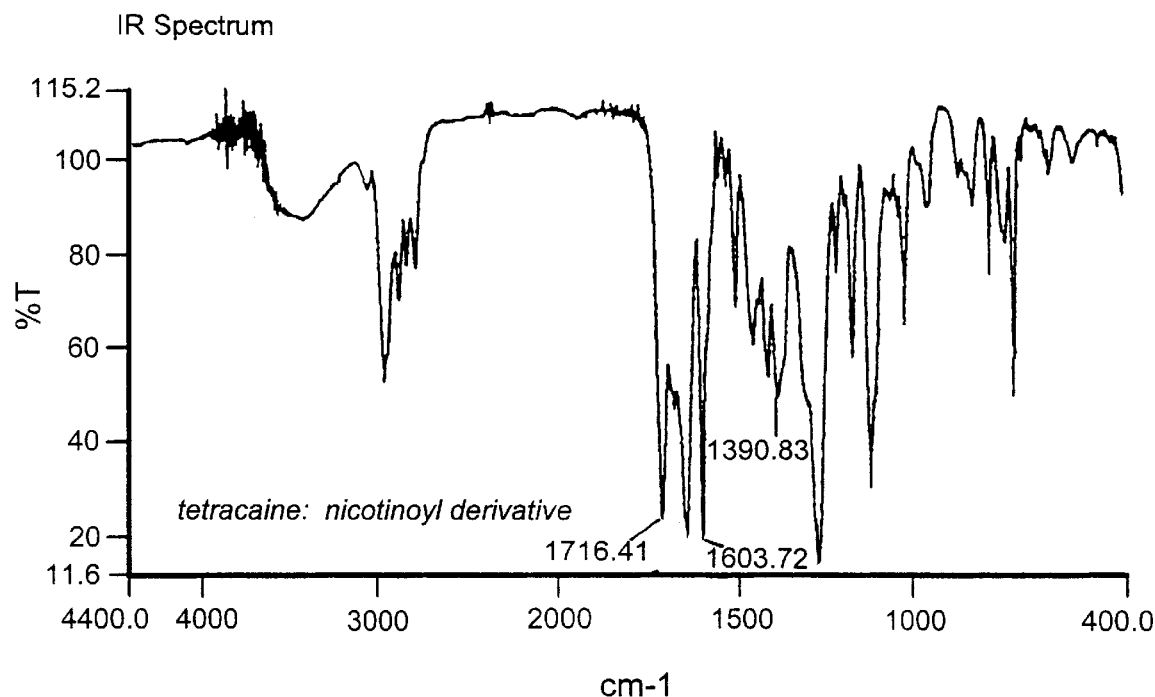
FIG. 6 Nicotinoyl derivative IR spectrum and structure.
Figure 6:
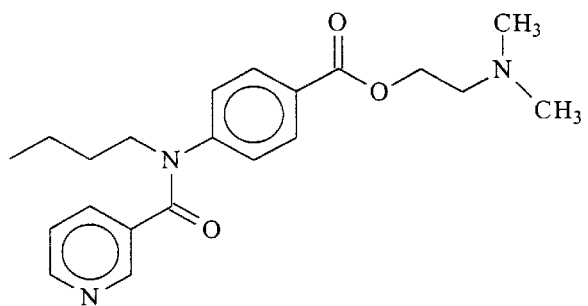

The subject invention pertains to novel materials and methods useful for providing long-acting local anesthesia. In a particularly preferred embodiment, the compounds of the subject invention are N-acyl derivatives of tetracaine. In a specific embodiment, the compounds of the subject invention can be represented by the following formula.

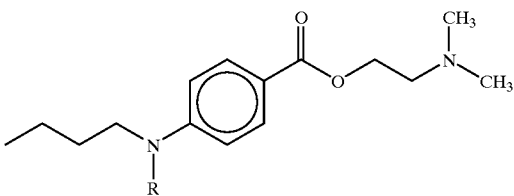

wherein R is

wherein R' is an alkyl chain $(CH_2)_n CH_3$, wherein n is from 1 to 22. The alkyl chain can be saturated or unsaturated. In addition, the alkyl chain can be straight or branched and can contain alicyclic as well as aromatic moieties. In a specific example R' is 3-pyridyl.

Further aspects of the subject invention pertain to the synthesis and use of the N-acyl derivatives of tetracaine. Tetracaine, itself, does not have properties which would make it useful as a long-acting local anesthetic.

Unexpectedly, it has been determined that by acylating the N-acyl moiety of tetracaine, there are obtained N-acyl derivatives of tetracaine which have valuable properties. These properties make the compounds of the invention useful as long-acting local anesthetics.

In a specific embodiment, the synthesis of the tetracaine derivatives of the subject invention can be done by mixing equimolar amounts of tetracaine base and an acyl chloride in acetonitrile, stirring at 23° C. for 15 minutes, and evaporating the solvent. This method gives an essentially quantitative yield of the desired product. In contrast, adding a proton scavenger such as triethylamine or pyridine results in the production of about 20% of a 3'-acyl derivative which is difficult to separate from the desired product.

The compounds of the subject invention can be administered in any of the variety of ways known to those skilled in the art. For example, sustained-release formulations are particularly suitable for the management of chronic pain. Arthritis is one condition for which sustained release formulations can be used. Suitable sustained-release formulations are described in, for example, EP-A-0309157.

Conventional, or immediate, release formulations may also be used to administer the subject compounds particularly for rapid-onset analgesia. Examples of suitable formulations include oral formulations, for example, tablets, capsules, solutions, suspensions, gels etc; nasal sprays and aerosols; inhalers; rectal systems, for example, suppositories, enemas, foams etc; liquids; injectables, for example, for intravenous, subcutaneous, intramuscular, intra-synovial use etc; and topical forms, for example, creams, ointments, gels and patches.

Irrespective of the kind of formulation used, the formulation can include a number of excipients in addition to the drug. Examples of such excipients, for use in oral tablets and capsules in particular, include fillers or bulking agents such as lactose, sorbitol, sucrose, mannitol and cellulose; binders such as polyvinylpyrollidone; disintegrants such as starch or EXPLOTAB®; lubricants such as magnesium stearate; coatings such as sugar-based materials, or films such as hydroxymethyl cellulose; flavours and/or sweeteners such as phenylalanine and saccharin; and colourings such as titanium dioxide or iron oxides. Such excipients are typically used in their standard amounts.

The compounds of the subject invention can be the sole pharmaceutically-active agent in a drug formulation. Alternatively, these compounds can be combined with other pharmaceutically-active agents, such as a gastroprotectant, for example, misoprostol or cyclodextrins; analgesics, for example opiates or paracetamol; NSAIDs; adjuvants, for example caffeine; or cough-cold remedies, for example, anti-histamines or sedatives.

Often, the aerosolization of a formulation for inhalation into the lung will require a propellent. The propellant may be any propellant generally used in the art. Examples of such useful propellants include but are not limited to a chloroflourocarbon, a hydrofluorocarbon, a hydochlorofluorocarbon,or a hydrocarbon, including trifluoromethane, dichlorodiflouromethane, dichlorotetrafluoroethanol, and 1,1,1,2-tetraflouroethane, or combinations thereof.

Systems of aerosol delivery, such as the pressurized metered dose inhaler and the dry powder inhaler are disclosed in Newman, S. P., *Aerosols and the Lung*, Clarke, S. W. and Davia, D. editors, pp. 197–22 and can be used in connection with the present invention.

The dosage is administered as needed. One of ordinary skill in the art can readily determine a volume or weight of the formulation corresponding to this dosage based on the concentration of anesthetic in the formulation of the invention.

In one embodiment, the present invention provides formulations and dosage forms for use in treating subjects suffering from pain. In general liquid dosage forms contain the subject anesthetics in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0–8.0 range, or water.

The formulation of the present invention may include, as optional ingredients, pharmaceutically acceptable carriers, diluents, solubilizing or emulsifying agents, surfactants and excipients.

The carrier may be a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

Following are examples which illustrate procedures for practicing the invention. These examples should not be construed as limiting. All percentages are by weight and all solvent mixture proportions are by volume unless otherwise noted.

EXAMPLE 1

N-acetyl tetracaine

Tetracaine base (10 mmol) is dissolved in acetonitrile (20 ml). Acetyl chloride (10 mmol) is added and the solution is stirred at room temperature for 15 minutes. The solvent is removed in vacuo at 30° C. The product is a pale yellow oil.

EXAMPLE 2

N-butyryl tetracaine

Tetracaine base (10 mmol) is dissolved in acetonitrile (20 ml). Butyryl chloride (10 mmol) is added and the solution is stirred at room temperature for 15 minutes. The solvent is removed in vacuo at 30° C. The product is a pale yellow oil.

EXAMPLE 3

N-hexanoyl tetracaine

Tetracaine base (10 mmol) is dissolved in acetonitrile (20 ml). Hexanoyl chloride (10 mmol) is added and the solution is stirred at room temperature for 15 minutes. The solvent is removed in vacuo at 30° C. The product is pale yellow oil.

EXAMPLE 4

N-decanoyl tetracaine

Tetracaine base (10 mmol) is dissolved in acetonitrile (20ml). Decanoyl chloride (10 mmol) is added and the solution is stirred at room temperature for 15 minutes. The solvent is removed in vacuo at 30° C. The product is a pale yellow oil.

EXAMPLE 5

N-nicotinoyl tetracaine

Tetracaine base (10 mmol) is dissolved in acetonitrile (20 ml). Nicotinoyl chloride, hydrochloride salt (10 mmol) is added and the solution is stirred at room temperature for 15 minutes. The solvent is removed in vacuo at 30° C. The product is a pale yellow oil.

EXAMPLE 6

Infrared analysis

The oily product obtained from the above reaction is smeared on a potassium bromide pellet and the pellet is introduced into the sample chamber of a Fourier Transform IR spectrophotometer (Perkin Elmer 1000 Series). The IR spectra are computed using the PE Nelson Spectrum software. Results are reported in FIGS. 1 to 6. Evidence of correct structure can be seen in the disappearance of the N-H peak at 3369 cm-1 which is present in tetracaine (FIG. 1) as well as the appearance of a new peak at 1720 cm-1 and a shift of the 1685 peak to 1660 cm-1. Disappearance of the N-H peak indicates that substitution occurred on the 4'-nitrogen as desired. The 1720 cm-1 peak is typical of the carbonyl group of an amide moiety. If substitution had been on the benzene ring instead, then this band would have occurred at frequencies below 1700 cm-1 instead of 1720 cm-1.

EXAMPLE 7

HPLC traces

The test compounds are analyzed by HPLC in order to estimate their purity. The HPLC system consists of a Perkin Elmer binary pump Model 250, an Applied Biosystems Model 785A programmable detector set at 254 nm, a Rheodyne manual injector (100 μl loop), and a 0.3×3 cm RP C-18 column (3 μM). Solvent A is 0.1% trifluoroacetic acid (TFA) in acetonitrile. Solvent B is 0.1% TFA in water. The elution system is a linear gradient of 10 to 80% solvent A in 5 minutes, followed by 80% solvent A for another 5 minutes. The flow rate is 2.0 ml/min through the whole procedure. HPLC traces give essentially a single peak, with traces of other peaks adding to less than 5%. The retention times are as follows:

| | |
|---|---|
| Tetracaine: | 3.19 minutes |
| Acetyl derivative: | 2.77 minutes |
| Butyryl derivative: | 3.22 minutes |
| Hexanoyl derivative: | 3.76 minutes |
| Decanoyl derivative: | 4.98 minutes |
| Nicotinoyl derivative: | 2.60 minutes |

EXAMPLE 8

Effects on the tongue

The acetyl derivative (20 mg) is dissolved in 100% ethanol (0.1 ml) and water (0.9 ml) is added. The resulting cloudy suspension is deposited at the surface of the tongue and kept for at least 30 seconds before rinsing. Numbness of the tongue in the treated area develops within a few minutes.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of providing anesthesia, comprising administering to a patient an N-acyl derivative of tetracaine as an anesthetic.

* * * * *